US009757714B2

(12) United States Patent
Teunissen et al.

(10) Patent No.: US 9,757,714 B2
(45) Date of Patent: Sep. 12, 2017

(54) METHANATION PROCESS USING STABILIZED CATALYST SUPPORT COMPRISING TRANSITION ALUMINA

(71) Applicant: Haldor Topsøe A/S, Kgs. Lyngby (DK)

(72) Inventors: Herman Teunissen, Hillerød (DK); Thoa Thi Minh Nguyen, Lyngby (DK); Jens Sehested, Ballerup (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/763,914

(22) PCT Filed: Feb. 24, 2014

(86) PCT No.: PCT/EP2014/053541
§ 371 (c)(1),
(2) Date: Jul. 28, 2015

(87) PCT Pub. No.: WO2014/131728
PCT Pub. Date: Sep. 4, 2014

(65) Prior Publication Data
US 2015/0360209 A1    Dec. 17, 2015

(30) Foreign Application Priority Data

Feb. 27, 2013    (WO) ................. PCT/EP2013/053917

(51) Int. Cl.
*C07C 1/02*    (2006.01)
*C07C 1/04*    (2006.01)
(Continued)

(52) U.S. Cl.
CPC .............. *B01J 23/83* (2013.01); *B01J 21/04* (2013.01); *B01J 23/10* (2013.01); *B01J 23/755* (2013.01);
(Continued)

(58) Field of Classification Search
CPC . B01J 21/04; B01J 23/10; B01J 23/755; B01J 23/83; B01J 35/002; B01J 35/1004;
(Continued)

(56) References Cited

U.S. PATENT DOCUMENTS 3,962,140 A * 6/1976 Alcorn ................... B01J 23/885
502/315
2003/0032554 A1    2/2003 Park et al.
(Continued)

FOREIGN PATENT DOCUMENTS

CN    101884927 A  * 11/2010
EP    2 165 972 A2    3/2010
(Continued)

OTHER PUBLICATIONS

CN101884927A, Nov. 17, 2010, pp. 1-6; English translation.*
(Continued)

*Primary Examiner* — Medhanit Bahta
(74) *Attorney, Agent, or Firm* — Blank Rome LLP

(57) ABSTRACT

In a broad form the present disclosure relates to a stabilized catalyst support comprising in oxide form; aluminum, zirconium, and one or more lanthanoid elements taken from the lanthanoid group of the periodic system characterized in that at least a part of the aluminum is present as transition alumina such as $\chi$, $\kappa$, $\gamma$, $\delta$, $\eta$, $\rho$ and $\theta$-alumina, characterized in the concentration of zirconium being at least 1.5 wt %, 5 wt % or 10 wt %, the concentration of lanthanoid being at least 0.5 wt %, 1.0 wt %, 2 wt % or 4 wt % and the combined concentration of zirconium and lanthanoid being at least 4 wt %, 7 wt % or 10 wt %, with the associated benefit of a support comprising transition alumina being a high surface area due to the small crystallites typical for transition alumina, and the benefit of the combined presence of oxides of zirconium and lanthanoid in the stated amounts being that (Continued)

at these levels these oxides stabilize the structure of the transition alumina.

10 Claims, 2 Drawing Sheets

(51) Int. Cl.

| | |
|---|---|
| *C07C 1/10* | (2006.01) |
| *C07C 1/12* | (2006.01) |
| *B01J 23/83* | (2006.01) |
| *B01J 37/03* | (2006.01) |
| *B01J 21/04* | (2006.01) |
| *B01J 23/755* | (2006.01) |
| *B01J 35/00* | (2006.01) |
| *B01J 35/10* | (2006.01) |
| *B01J 37/00* | (2006.01) |
| *C01B 3/40* | (2006.01) |
| *C10G 2/00* | (2006.01) |
| *B01J 23/10* | (2006.01) |
| *C10L 3/08* | (2006.01) |
| *B01J 37/08* | (2006.01) |
| *B01J 37/10* | (2006.01) |
| *B01J 37/18* | (2006.01) |

(52) U.S. Cl.
CPC ......... *B01J 35/002* (2013.01); *B01J 35/1004* (2013.01); *B01J 37/0009* (2013.01); *B01J 37/031* (2013.01); *C01B 3/40* (2013.01); *C07C 1/0435* (2013.01); *C10G 2/33* (2013.01); *C10L 3/08* (2013.01); *B01J 35/006* (2013.01); *B01J 37/08* (2013.01); *B01J 37/10* (2013.01); *B01J 37/18* (2013.01); *B01J 2523/00* (2013.01); *C01B 2203/0233* (2013.01); *C01B 2203/0261* (2013.01); *C01B 2203/1058* (2013.01); *C01B 2203/1082* (2013.01); *C10L 2290/42* (2013.01); *Y02P 20/52* (2015.11)

(58) Field of Classification Search
CPC .. B01J 37/0009; B01J 37/031; B01J 2523/00; B01J 35/006; B01J 37/08; B01J 37/10; B01J 37/18; C01B 3/40; C01B 2203/0233; C07C 1/0435; C10G 2/33; C10L 3/08

See application file for complete search history.

(56) References Cited

U.S. PATENT DOCUMENTS

| | | | |
|---|---|---|---|
| 2010/0068130 A1* | 3/2010 | Wilhelm | ............... B01J 21/04 423/648.1 |
| 2013/0211148 A1 | 8/2013 | Schäfer et al. | |

FOREIGN PATENT DOCUMENTS

| | | | | |
|---|---|---|---|---|
| EP | 2 308 594 A2 | 4/2011 | | |
| WO | WO 02/087756 A1 | 11/2002 | | |
| WO | WO 2010006386 A2 * | 1/2010 | ............... | C07C 1/12 |
| WO | WO 2011/087467 A1 | 7/2011 | | |

OTHER PUBLICATIONS

Cai, M. et al. "Methanation of carbon dioxide on Ni/ZrO2—Al2O3 catalysts: Effects of ZrO2 promoter and preparation method of novel ZrO2—Al2O3 carrier" J. Nat. Gas. Chem. 2011, 20, pp. 318-324.*

* cited by examiner

METHANATION PROCESS USING STABILIZED CATALYST SUPPORT COMPRISING TRANSITION ALUMINA

BACKGROUND OF THE INVENTION

The invention relates to a catalyst having an improved stability against deactivation at high temperatures and high partial pressure of steam, which is especially suited for steam reforming processes and methanation processes, as well as a process for substitute national gas production.

Substitute Natural Gas (SNG) can be produced in large scale from coal via gasification and subsequent methanation of the produced synthesis gas in one or several reactors to achieve sufficiently high $CH_4$ content in the final product. The methanation step is often carried out in a series of adiabatic, fixed bed reactors, where the main reactions taking place are:

$$CO + H_2O = CO_2 + H_2 \quad (1)$$

$$CO + 3H_2 = CH_4 + H_2O \quad (2)$$

In the case of methanation from $CO_2$ and $H_2$, it is believed that the mechanism of the reaction goes first via reverse water gas shift (i.e., the reverse of reaction (1)), followed by CO methanation to form $CH_4$, so that the overall reaction is:

$$CO_2 + 4H_2 = CH_4 + 2H_2O \quad (3)$$

The methanation of synthesis gas is highly exothermic, which results in a large temperature increase in these reactors. Suitable catalysts for methanation thus need to be sufficiently active at low temperatures, resistant against sintering at high temperatures and high partial pressure of steam, and resistant to other deactivation phenomena, for example carbon formation. The catalyst sintering stability is most critical in the upstream reactors where the exit temperatures are the highest. The methanation process is typically carried out at elevated pressure (above 10 barg, potentially up to more than 100 barg) and at maximum temperatures between 500° C. and 750° C. with a partial pressure of steam between 2 and 15 barg, but potentially up to 30 barg.

The reverse process steam and/or oxygen reforming occurs under similar conditions in the presence of methane (and/or other hydrocarbons) and water.

A further high temperature process for which stabilization of catalyst and catalyst support is important is catalytic combustion of fuels, which may occur elevated pressures, at temperatures between 600° C. and 1000° C., and with water as a product in the case of fuels comprising hydrogen, e.g. according to (4) below.

$$CH_4 + 2O_2 = CO_2 + 2H_2O \quad (4)$$

In WO2011/087467 a catalyst comprising nickel on a support comprising alumina, zirconia and various combinations of cerium, praseodymium, and neodymium are described as reforming catalysts for fuel cells. The composition of the catalyst is not stated, but the nickel content is estimated to be above 60%, and the focus of the application is on the pore structure of the catalyst, which may be especially relevant for maintaining a well dispersed nickel phase at such a high metal concentration. The application does not consider the crystal structure of alumina or the mechanical stability of the catalysts, the catalytic activity is not demonstrated and pore structure stability is only demonstrated up to 450° C.

In WO2002/087756 a reforming catalyst comprising 3.7-16 wt % nickel on a support comprising 0.1-4.1 wt % lanthania, 0.1-2.2 wt % zirconia and magnesia/alumina of an unspecified crystal structure. The combined elemental content of La and Zr is 0.7-4.1 wt % in the support, and in all examples one of the two elements is present in a concentration below 0.5 wt %. The catalytic activity for methane steam reforming of the catalyst was tested at 750° C. at an unspecified pressure, and stability was not considered.

US 2003/032554 discloses a catalyst comprising 3-12 wt % nickel, theta-alumina and less than 5 wt % (relative to theta-alumina) of a theta-alumina modifying component, typically being a combination of zirconia and a lanthanoide such as lanthanum or cerium. All examples are based on catalyst comprising 0.9-1.0 wt % $La_2O_3$ or $CeO_2$, 2.3-2.5 wt % $ZrO_2$ and 2.8-12.5 wt % Ni, or catalysts further comprising calcium, magnesium and/or cesium. The combined elemental content of La, Ce and Zr is 3.6 wt % in the catalyst support. The catalytic activity for methane steam reforming of the catalyst was tested at 750° C. at atmospheric pressure, and long term stability was not considered.

Therefore based on the prior art there is no indication of the importance of stabilizing the surface area of the catalyst support at high temperatures, especially in the presence of steam, nor an indication of the stabilization of transition alumina in catalyst supports as a way to obtain a stable surface area.

Well known catalysts for methanation processes contain Ni as the active phase, which provide the highest methanation activity per unit cost, on a stabilized support containing high surface area $Al_2O_3$. At high temperatures, especially in the presence of steam high surface area transition $Al_2O_3$ (e.g. $\chi$, $\kappa$, $\gamma$, $\delta$, $\eta$, $\rho$ and $\theta$-$Al_2O_3$) tends to sinter and transform towards the thermodynamically more stable $\alpha$-$Al_2O_3$ phase, leading to a loss of surface area due to the collapse of the carrier and a reduction in catalyst pellet mechanical strength. The loss of surface area can be so severe that the Ni particles also sinter together, leading to a loss of catalytic activity. The reduction in the mechanical strength can be so severe that the catalyst pellets crumble into dust during operation or unloading.

SUMMARY OF THE INVENTION

Now, according to the present disclosure, a catalyst support, a reforming catalyst and a methanation catalyst with improved stability is provided according to which, the transition $Al_2O_3$ carrier is stabilized against phase transformation by introducing of both a refractory oxide such as $ZrO_2$ and an element from the lanthanoid group of the periodic system such as La into the catalyst support or carrier, and to include both of these constituents in amounts sufficient for influencing stability, i.e. above 0.5 wt % lanthanoid, above 1.5 wt % zirconium and at least 4 wt % in combination.

As it is well known to the skilled person, a catalyst actine in methanation is also active in the reverse reforming process, which is also active at elevated temperatures. Therefore a steam reforming catalyst being stabilized against deactivation will similarly be attractive.

In the following the elemental concentrations of metals designated by %, wt % or wt/wt %, including nickel, zirconia and lanthanoid oxides shall be understood as the weight fractions of elemental metal, relative to the total mass of catalyst, or relative to the mass of catalyst support (i.e. excluding the active material nickel) if stated.

In the following the terms catalyst support and carrier shall be construed as synonyms. Both terms shall refer to the structural support of the catalyst, which has a wide range of important characteristics known to the person skilled in the art, including the provision of a high surface area for the active material (such as nickel or noble metals) dispersed on the catalyst support.

Alumina, $Al_2O_3$, may be present in many crystal forms, which are often simply designated "alumina" for the stable crystal form $\alpha$-$Al_2O_3$ and "transition-alumina" for thermodynamically metastable crystal forms such as $\chi$, $\kappa$, $\gamma$, $\delta$, $\eta$, $\rho$ and $\theta$-alumina. Transition aluminas typically have higher surface areas, but are known to degrade to thermodynamically stable $\alpha$-$Al_2O_3$ at elevated temperatures and under increased steam partial pressure. Where the term transition alumina is used in the following it shall cover any form of high surface area alumina other than the thermodynamically stable $\alpha$-$Al_2O_3$.

The relative amount of $\alpha$-$Al_2O_3$ represents the fraction of $\alpha$-$Al_2O_3$ in the total $Al_2O_3$ carrier as determined by x-ray diffraction (XRD) by the mathematical technique Rietveld refinement, well-known to those skilled in the art.

The relative surface area is the surface area normalized by the corresponding value in the fresh catalyst A, as measured by BET.

The relative intrinsic methanation activity is the methanation activity normalized by the corresponding value in the fresh catalyst A.

The term "in oxide form" as e.g. aluminum, zirconium, and one or more lanthanoid elements "in oxide form" shall be understood as non-limiting in terms of the specific oxide form, which may thus be as combinations of the individual oxides $Al_2O_3$, $ZrO_2$, $La_2O_3$, etc. or as binary oxides such as $LaAlO_3$.

In alignment with the terminology of the person skilled in the art the term pore stabilization shall be construed as a stabilization of the structure of the pores in the catalyst support, where the term structural stabilization is used this shall be construed as stabilization of the crystalline structure.

In a broad form the present disclosure relates to a stabilized catalyst support comprising in oxide form; aluminum, zirconium, and one or more lanthanoid elements taken from the lanthanoid group of the periodic system characterized in that at least a part of the aluminum is present as transition alumina such as $\chi$, $\kappa$, $\gamma$, $\delta$, $\eta$, $\rho$ and $\theta$-alumina, characterized in the concentration of zirconium being at least 1.5 wt %, 5 wt % or 10 wt %, the concentration of lanthanoid being at least 0.5 wt %, 1.0 wt %, 2 wt % or 4 wt % and the combined concentration of zirconium and lanthanoid being at least 4 wt %, 7 wt % or 10 wt %, with the associated benefit of a support comprising transition alumina having a high surface area due to the small crystallites typical for transition alumina, and the benefit of the combined presence of oxides of zirconium and lanthanoid in the stated amounts being that at these levels these oxides stabilize the structure of the transition alumina.

In a further embodiment the fraction of alumina in the support being $\chi$, $\kappa$, $\gamma$, $\delta$, $\eta$, $\rho$ or $\theta$-alumina is at least 0.1, 0.4 or 0.6, with the associated benefit of the alumina being $\chi$, $\kappa$, $\gamma$, $\delta$, $\eta$, $\rho$ or $\theta$-alumina, i.e. a transition alumina is that the crystallites of transition alumina are small, and thus have high surface area, and thereby will provide the possibility for a highly catalytically active material, by stabilizing the high dispersion of catalytically active material.

In a further embodiment the elemental concentration in the catalyst support of the one or more lanthanoid elements present as oxide is below 4 wt %, 8 wt % or 10 wt % with the associated benefit of a balance between the structural stabilization effect and the increased cost due to expensive lanthanoid.

In a further embodiment the elemental concentration of zirconium is below 25 wt % or 50 wt % with the associated benefit of a balance between the structural stabilization effect and the increased cost due to expensive zirconium, as well as a the benefit of not reducing the surface area in the presence of excessive amounts of zirconia.

In a more specific manner the present disclosure relates to a catalyst comprising nickel on a support comprising, in oxide form; aluminum, zirconium, and one or more lanthanoid elements taken from the lanthanoid group of the periodic system characterized in that at least a part of the aluminum is present as transition alumina with the associated benefit of said catalyst achieving an increased catalyst lifetime by an improved stability against sintering, due to stabilization of transition alumina.

In a further embodiment the concentration of nickel in the catalyst is 5-80 wt %, preferably 10-50 wt %, and most preferably 15-30 wt % with the associated benefit of said catalyst having high activity.

In a further embodiment the fraction of alumina in the catalyst being $\alpha$-alumina is less than 0.9, preferably less than 0.6 and most preferably less than 0.4, with the associated benefit of the remainder of the alumina being a transition alumina having a high surface area, and thus provides a highly catalytically active material, by stabilizing the high dispersion of nickel.

In a further embodiment the elemental concentration in the catalyst of the lanthanoid present as oxide is 0.1-10 wt %, more preferably 0.5-8 wt % and most preferably 1-4 wt %, with the associated benefit of being an optimal balance between cost and stabilizing effect of said lanthanoid element.

In a further embodiment the lanthanoid in the catalyst or the catalyst support is taken from the group consisting of lanthanum, cerium, praseodymium, samarium, gadolinium, neodymium, europium, dysprosium and ytterbium with the associated benefit of said lanthanoid being effective in stabilization of transition alumina against transformation to $\alpha$-$Al_2O_3$ and thus sintering.

In a further embodiment the elemental concentration in the catalyst of zirconium is from 1 wt %, 2 wt %, 3 wt % or 5 wt % to 10 wt %, 25 wt %, 35 wt % or 50 wt %, with the associated benefit of said zirconium concentrations providing an effective stabilization of transition alumina in synergy with lanthanoids while ensuring the catalytic activity, and while avoiding excessive cost due to a high concentration of expensive raw materials.

In a further embodiment the catalyst or the catalyst support further comprises magnesium in an oxide form, in which the elemental concentration of magnesium preferably is 1-30 wt %, and more preferably 4-14 wt % with the associated benefit of stabilizing the support further, preferably in a spinel form.

A further aspect of the invention relates to the use of such a catalyst for methanation or steam reforming.

A further aspect of the invention relates to a process for producing a gas comprising methane by reacting a synthesis gas comprising carbon oxide and hydrogen in the presence of a catalyst comprising such a catalyst support or such a catalyst.

In a further embodiment the temperature of the synthesis gas prior to contacting the catalytically active material is from 300° C. or 400° C. to 500° C., 600° C. or 700° C. with the associated benefit of the temperatures being sufficient for activating the methanation reaction, while avoiding that the catalyst is damaged by sintering or high temperature carbon formation.

In a further embodiment the temperature increase of the gas comprising methane after contacting the catalytically actine material is at least 50° C.

In a further embodiment the synthesis gas prior to contacting the catalytically active material has a module i.e. a molar ratio $M=(H_2-CO_2)/(CO+CO_2)$ between 1 and 20, preferably between 2 and 5 and most preferably between 3 and 3.5, with the associated benefit of the reaction being well balanced with a low risk for side reactions, and a composition matching production of high quality synthetic natural gas.

A further aspect of the present disclosure relates to a process for producing a synthesis gas from a gas rich in hydrocarbons by steam and/or oxygen reforming, involving reacting the gas rich in hydrocarbons with water and/or oxygen in the presence of a catalyst or a catalyst comprising a catalyst support according to the present disclosure, with the associated benefit that the catalyst crystal structure is stable and providing a high surface area even at elevated steam partial pressure and temperature.

In a further embodiment the gas rich in hydrocarbons prior to contacting the catalytically active material is from 350° C. or 550° C. to 600° C., 1000° C. or 1200° C. with the associated benefit of providing an efficient production of hydrogen from water and/or oxygen and hydrocarbons. The temperatures may reflect adiabatic pre-reforming conditions (350° C. to 600° C.) under consumption of especially higher hydrocarbons by reaction with water, steam reforming conditions (600° C. to 1000° C.) under consumption of especially methane by reaction with water, and oxygen reforming conditions (800° C. to 1200° C.) under consumption of hydrocarbons by reaction with water and/or oxygen.

DETAILED DESCRIPTION OF THE INVENTION

Figure 1:
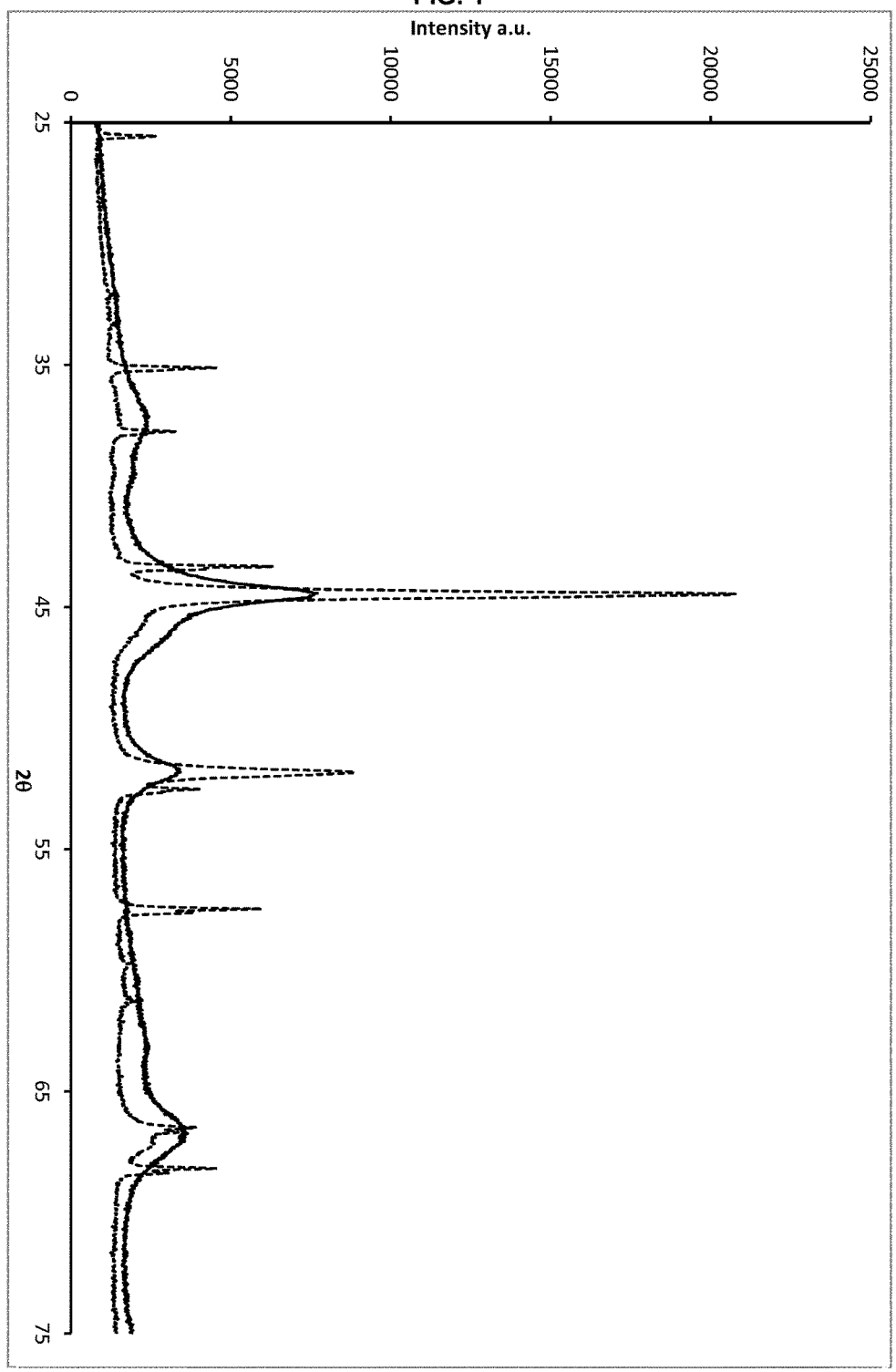
FIG. 1 is an XRD diagram illustrating the crystal structure of Catalyst A before and after aging.

According to the present disclosure, a methanation catalyst with improved stability is provided according to which, the $Al_2O_3$ carrier is stabilized against phase transformation by introducing of both a refractory oxide such as $ZrO_2$ and an element from the lanthanoid group of the periodic system such as La into the carrier. Without being bound by theory the effect of $ZrO_2$ is assumed to be two-fold, both to hinder phase transformation towards $\alpha$-$Al_2O_3$ and to increase the mechanical strength of the shaped bodies. Also without being bound by theory, the lanthanoid is assumed to work as a promoter to minimize the phase transformation of high surface area $Al_2O_3$ and to improve the catalytic activity.

The manufacturing methodology for the catalysts of the present invention is based on creating intimate contact between the components involved, either on nanometer scale or on micrometer scale. Thus, the catalysts of the present invention can be produced by any method known in the art which renders an effective mixture of the individual components. This may involve precipitation of a single constituent, or co-precipitation of multiple constituents, which methods are described in more detail in Synthesis of Solid Catalysts, edited by Krijn de Jong, 2009 WILEY-VCH Verlag GmbH & Co. KGaA, Weinheim. Alternatively, the preparation might involve mixing of constituent(s) followed by extrusion or high energy milling in the dry or wet phase. High energy milling may be carried out using a range of methods, of which some are disclosed in section 2.4 of Mechanochemistry in Nanoscience and Minerals Engineering by Peter Balaz, Springer 2008.

Suitable precursors comprise water soluble salts of the constituents, in the case of (co)precipitation. Furthermore oxides, hydroxides, carbonates, basic carbonates and mixtures thereof are suitable materials for mixing, extrusion and high energy milling. These examples should be understood as illustrations rather than limitations of the present inventions. The mixing steps are usually followed by drying steps, optionally preceded by filtration as in the case of (co) precipitation.

After drying, the mixtures are transformed into so-called green bodies by a shaping method such as tabletizing. Alternatively the green bodies comprise the extrudates, which are obtained prior to the drying step. The green bodies may be fired under air, other $O_2$ containing gases, nitrogen or other inert gasses at temperatures of 600-1200° C. after which the active Ni catalyst is obtained by a reduction treatment using dihydrogen at elevated temperatures of 500-1000° C. As known to the person skilled in the art, transition alumina as such is unstable at temperatures above 1050° C., but if alumina is modified by a stabilizer such as lanthania, zirconia or nickel oxide firing at higher temperatures is not a problem. Firing must also be made at elevated temperatures (600-1200° C.) to ensure that at least one of the stabilizing zirconium and lanthanoid oxides are structurally integrated in the transition alumina, and thereby providing a stabilized crystal structure.

In one aspect of the present disclosure the green body consists of some of said components and the addition of the remaining components may be carried out by an impregnation step comprising at least one aqueous solution containing said component(s) in dissolved state. Impregnation steps are followed by thermal treatment e.g. calcination and finally reduction. Optionally, the impregnation steps are preceded by calcination at 600-1200° C. Impregnation may be made with one or more component solutions of appropriate purity or a mixture of components of limited purity dependent on the desired catalyst quality, cost and other practical issues.

The assessment of catalyst stability involved an aging procedure in combination with an evaluation of the aged catalyst.

The accelerated lab aging procedure involved exposing the fresh catalyst to high temperatures and high steam partial pressures in the laboratory. Relevant catalysts were used as whole pellets and subjected to a gas consisting of steam and hydrogen in high levels 30 barg, 670° C. for 2 weeks. These conditions are not often found in normal operation, but it allows the investigation of the long term sintering stability in a relatively short time in the laboratory. The relevant catalysts are then analyzed for various properties after the aging procedure. A similar procedure was also carried out for inactive catalyst supports, to evaluate physical and structural parameters of the catalyst supports.

The evaluation of the activity of the aged catalyst was made by determining the intrinsic methanation activity of the fresh and aged catalysts under the same operating condition: the relevant catalyst was crushed to 0.1-0.3 mm fraction and diluted with an appropriate inert also crushed to the same fraction such that the catalyst weight fraction in the mixture was approximately 4%. The reason to mix the catalyst with inert was to limit the conversion inside the catalyst bed and obtain the most representative intrinsic activity measurements. One gram of the catalyst and inert mixture was loaded in a fixed bed reactor and exposed to approximately 10 L/h of a gas containing 10% CO and 90% $H_2$. The exit gas was analyzed for composition using a standard gas chromatograph.

The temperature inside the reactor was monitored both inside the catalyst bed and on the reactor wall. The catalyst activity may thus be calculated from the $CH_4$ produced and the CO and $H_2$ consumed. The intrinsic activity was measured several times at the same temperature, and was measured from 275 to 325° C. Under these conditions, it was confirmed that there was insignificant temperature increase through the catalyst bed, as well as insignificant mass and heat transfer limitations such that the effectiveness of the catalyst particles was close to 1. This means that the measured catalyst activity was the true intrinsic methanation activity.

A simpler assessment of the stability of the catalyst was the determination of the relative amount of alumina which was present as α-alumina by XRD. For the present examples the fresh catalyst had a relative amount of α-alumina of 0, and this increases with sintering; in some cases to 1, corresponding to full conversion of transition alumina to α-alumina.

The determination of the distribution between crystal structures by XRD is based on analysis by Rietveld refinement of XRD diagrams such as shown in FIG. 1. FIG. 1 illustrates the crystal structure of Catalyst A before (solid line) and after (dashed line) aging. As it is well known to the person skilled in the art the XRD for large crystal α-alumina is characterized by sharp peaks, whereas transition alumina having small crystallites, like γ-$Al_2O_3$ in this case, are characterized by broad soft "bumps". Catalyst A does not comprise zirconia or lanthania, so only alumina peaks are visible.

EXAMPLE 1

Eight catalysts containing Ni on a high surface area γ-$Al_2O_3$ support were prepared using the following method.

Catalyst A according to the prior art was prepared as follows:

Commercial high surface area transition alumina extrudates (primary gamma alumina), were used as a catalyst carrier. The extrudates were impregnated with an aqueous $Ni(NO_3)_2$ solution, calcined under air at 450° C. and reduced under a flow of $H_2$ at 600° C.

Catalyst A consisted of 31 wt % Ni on a high surface area transition $Al_2O_3$ support.

Catalyst B according to the prior art was prepared from Catalyst A, by impregnation of the calcined NiO containing extrudates with an aqueous $La(NO_3)_3$ solution. The final catalyst was then obtained after further calcination and reduction as mentioned above.

Catalyst B consisted of 30 wt % Ni on a high surface area transition $Al_2O_3$ support, and stabilized by 2.5 wt % La as $La_2O_3$. The amount of La relative to the support was 3.6 wt %.

Catalyst C according to the prior art was prepared from an aqueous suspension containing Al (as böhmite), Zr (as hydroxide) and Ni (as basic carbonate). The suspension was dried and the powder was pressed into tablets after addition of graphite. The tablets were calcined in air at 925-1000° C. and reduced with $H_2$ up to 840° C.

Catalyst C consisted of 23 wt % Ni on a high surface area transition $Al_2O_3$ support, stabilized by 21 wt % Zr as $ZrO_2$. The amount of Zr relative to the support was 27 wt %.

Catalyst D according to the present disclosure was prepared from Catalyst C by impregnation of the calcined tablets with an aqueous $La(NO_3)_3$ solution. The final catalyst was then obtained after calcination at 450° C. and reduction up to 840° C., as mentioned above.

Catalyst D consisted of 23 wt % Ni on a high surface area transition $Al_2O_3$ support, stabilized by 2.1 wt % La as $La_2O_3$ and 21 wt % Zr as $ZrO_2$. The amount of La and Zr relative to the support was 2.7 wt % and 27 wt % respectively.

Catalyst E according to the present disclosure was prepared from Catalyst C by impregnation with an aqueous $Pr(NO_3)_3$ solution. The final catalyst was then obtained as mentioned above for Catalyst D.

Catalyst E comprises 23 wt % Ni on a high surface area transition $Al_2O_3$ support, stabilized 2 wt % by Pr as $Pr_6O_{11}$ and 21 wt % Zr as $ZrO_2$. The amount of Pr and Zr relative to the support was 2.6 wt % and 27 wt % respectively.

Catalyst F according to the present disclosure was prepared from Catalyst C by impregnation with an aqueous $Ce(NO_3)_3$ solution. The final catalyst was then obtained as mentioned above for Catalyst D.

Catalyst F comprises 23 wt % Ni on a high surface area transition $Al_2O_3$ support, stabilized by 1.6 wt % Ce as $CeO_2$ and 21 wt % Zr as $ZrO_2$. The amount of Ce and Zr relative to the support was 2.1 wt % and 27 wt % respectively.

Catalyst G according to the present disclosure was prepared from Catalyst C according to the procedure of Catalyst D. Catalyst G consisted of 23 wt % Ni on a high surface area transition $Al_2O_3$ support, stabilized by 1.1 wt % La as $La_2O_3$ and 21 wt % Zr as $ZrO_2$. The amount of La and Zr relative to the support was 1.4 wt % and 27 wt % respectively.

Catalyst H according to the present disclosure was prepared from Catalyst C according to the procedure of Catalyst D. Catalyst H consisted of 23 wt % Ni on a high surface area transition $Al_2O_3$ support, stabilized by 0.5 wt % La as $La_2O_3$ and 21 wt % Zr as $ZrO_2$. The amount of La and Zr relative to the support was 0.7 wt % and 28 wt % respectively.

The properties of the catalysts after the accelerated lab aging procedure are shown in Table 1. It can be seen that the procedure induces a large degree of both Ni and carrier sintering, in that the aged catalyst has a large Ni crystallite size, hence a significant reduction in the intrinsic methanation activity, and that the high surface area transition $Al_2O_3$ carrier has been transformed into α-$Al_2O_3$, leading to the loss of surface area.

It is also seen that both $La_2O_3$ and $ZrO_2$ stabilize the transition $Al_2O_3$, and that the stabilization in the two catalysts with $ZrO_2$ in combination with either $La_2O_3$ or $Pr_6O_{11}$ is even higher that what would be expected from the stabilization by one of these. To the extent that experimental data was available it was confirmed that this increased stability of transition $Al_2O_3$ was reflected as increased intrinsic methanation activity.

TABLE 1

Properties of fresh and lab-aged catalysts. The relative α-$Al_2O_3$ represents the weight fraction of α-$Al_2O_3$ relative to the total amount of $Al_2O_3$ in the carrier, as measured by XRD.

| Catalyst | | Ni crystallite size (Å)[1] | Relative α-$Al_2O_3$ (wt/wt) | Relative surface area BET | Relative intrinsic methanation activity |
|---|---|---|---|---|---|
| Catalyst A | Fresh | 80 | 0 | 1 | 1 |
| Ni/$Al_2O_3$ | Aged | 728 | 1 | 0.05 | 0.04 |
| Catalyst B | Fresh | | 0 | | |
| Ni/$Al_2O_3$/$La_2O_3$ | Aged | 333 | 0.36 | | |
| Catalyst C | Fresh | 180 | 0 | 0.20 | 0.27 |
| Ni/$Al_2O_3$/$ZrO_2$ | Aged | 324 | 0.53 | 0.09 | 0.08 |
| Catalyst D | Fresh | 120 | 0 | 0.26 | 1 |
| Ni/$Al_2O_3$/$La_2O_3$/$ZrO_2$ | Aged | 240[2] | 0.04[3] | 0.16 | 0.30 |

TABLE 1-continued

Properties of fresh and lab-aged catalysts. The relative α-Al₂O₃ represents the weight fraction of α-Al₂O₃ relative to the total amount of Al₂O₃ in the carrier, as measured by XRD.

| Catalyst | | Ni crystallite size (Å)[1] | Relative α-Al₂O₃ (wt/wt) | Relative surface area BET | Relative intrinsic methanation activity |
|---|---|---|---|---|---|
| Catalyst E | Fresh | | 0 | | |
| Ni/Al₂O₃/Pr₆O₁₁/ZrO₂ | Aged | 225[2] | 0.09[3] | | 0.31 |
| Catalyst F | Fresh | | 0 | | |
| Ni/Al₂O₃/CeO₂/ZrO₂ | Aged | 240 | 0.06[3] | | 0.28 |
| Catalyst G | Fresh | | 0 | | |
| Ni/Al₂O₃/La₂O₃/ZrO₂ | Aged | 226 | 0.20 | | 0.21 |
| Catalyst H | Fresh | | 0 | | |
| Ni/Al₂O₃/La₂O₃/ZrO₂ | Aged | 233 | 0.27 | | 0.14 |

[1]Measured using XRD
[2]Corrected value
[3]Corresponding to <0.1.

EXAMPLE 2

Further 12 high surface area catalyst supports were prepared using the following method. As it will be appreciated by the person skilled in the art, stability of the support will not be negatively affected by the presence of active constituents such as nickel.

Support I

A mixture of 36 g HNO₃ (65 wt %) and 605 g water is added to 1000 g Böhmite and mixed thoroughly at 65° C. using a mixer such as a z-mixer. Then, the mixture is extruded and the extrudates are calcined at 500° C. The calcined extrudates are crushed, mixed with water and magnesium stearate, and tabletized. Finally, the tablets are calcined at 1150° C. for 2 h. Support I consisted of pure Al₂O₃.

Support J

Support J was prepared according to the procedure of support I using 36 g HNO₃ (65 wt %), 617 g water, 974 g Böhmite and 26 g Zirconium hydroxide. Support J consisted of 97.5 wt % Al₂O₃ stabilized by 1.9 wt % Zr as ZrO₂.

Support K

Support K was prepared according to the procedure of support I using 36 g HNO₃ (65 wt %), 651 g water, 949 g Böhmite and 51 g Zirconium hydroxide. Support K consisted of 95.0 wt % Al₂O₃ stabilized by 3.7 wt % Zr as ZrO₂.

Support L

Support L was prepared according to the procedure of support I using 36 g HNO₃ (65 wt %), 649 g water, 889 g Böhmite and 111 g Zirconium hydroxide. Support L consisted of 89.2 wt % Al₂O₃ stabilized by 8.0 wt % Zr as ZrO₂.

Support M

Support M was prepared according to the procedure of support I using 36 g HNO₃ (65 wt %), 643 g water, 753 g Böhmite and 247 g Zirconium hydroxide. Support M consisted of 75.9 wt % Al₂O₃ stabilized by 17.9 wt % Zr as ZrO₂.

Support N

Support N was prepared according to the procedure of support I using 29 g HNO₃ (65 wt %), 417 g water, 544 g Böhmite and 339 g Zirconium hydroxide. Support N consisted of 62.3 wt % Al₂O₃ stabilized by 27.9 wt % Zr as ZrO₂.

Support O

The uncalcined tablets, obtained as Support I were impregnated with an aqueous La(NO₃)₃ solution to obtain a La content of 4 wt %. Finally, the tablets are calcined at 1150° C. for 2 h. Support O consisted of 95.3 wt % Al₂O₃, stabilized by 4 wt % La as La₂O₃.

Support P

The uncalcined tablets, obtained as Support J were converted to Support P according to the procedure of support O. Support P consisted of 93.0 wt % Al₂O₃ stabilized by 1.8 wt % Zr as ZrO₂ and 4 wt % La as La₂O₃.

Support Q

The uncalcined tablets, obtained as Support K were converted to Support Q according to the procedure of support O. Support Q consisted of 90.6 wt % Al₂O₃ stabilized by 3.5 wt % Zr as ZrO₂ and 4 wt % La as La₂O₃.

Support R

The uncalcined tablets, obtained as Support L were converted to Support P according to the procedure of support O. Support R consisted of 85.1 wt % Al₂O₃ stabilized by 7.6 wt % Zr as ZrO₂ and 4 wt % La as La₂O₃.

Support S

The uncalcined tablets, obtained as Support M were converted to Support S according to the procedure of support O.

Support S consisted of 72.3 wt % Al₂O₃ stabilized by 17.0 wt % Zr as ZrO₂ and 4 wt % La as La₂O₃.

Support T

The uncalcined tablets, obtained as Support N were converted to Support T according to the procedure of support O.

Support I consisted of 59.4 wt % Al₂O₃ stabilized by 26.6 wt % Zr as ZrO₂ and 4 wt % La as La₂O₃.

TABLE 2

Composition and properties of fresh and lab-aged supports. The relative α-Al₂O₃ represents the weight fraction of α-Al₂O₃ relative to the total amount of Al₂O₃ in the carrier, as measured by XRD.

| Support | Zr wt % | La wt % | Relative α-Al₂O₃ (wt/wt) | |
|---|---|---|---|---|
| | | | fresh | aged |
| I | 0 | 0 | 0.96 | 0.96 |
| J | 1.9 | 0 | 0.95 | 0.98 |
| K | 3.7 | 0 | 0.95 | 0.96 |
| L | 8.0 | 0 | 0.92 | 0.98 |
| M | 17.9 | 0 | 0.95 | 0.94 |
| N | 27.9 | 0 | 0.61 | 0.96 |
| O | 0 | 4 | 0.05[1] | 0.36 |
| P | 1.8 | 4 | 0.04[1] | 0.20 |
| Q | 3.5 | 4 | 0.04[1] | 0.09[1] |
| R | 7.6 | 4 | 0.04[1] | 0.08[1] |
| S | 17.0 | 4 | 0.06[1] | 0.09[1] |
| T | 26.6 | 4 | 0.07[1] | 0.06[1] |

[1]<0.1 alpha alumina.

Figure 2:
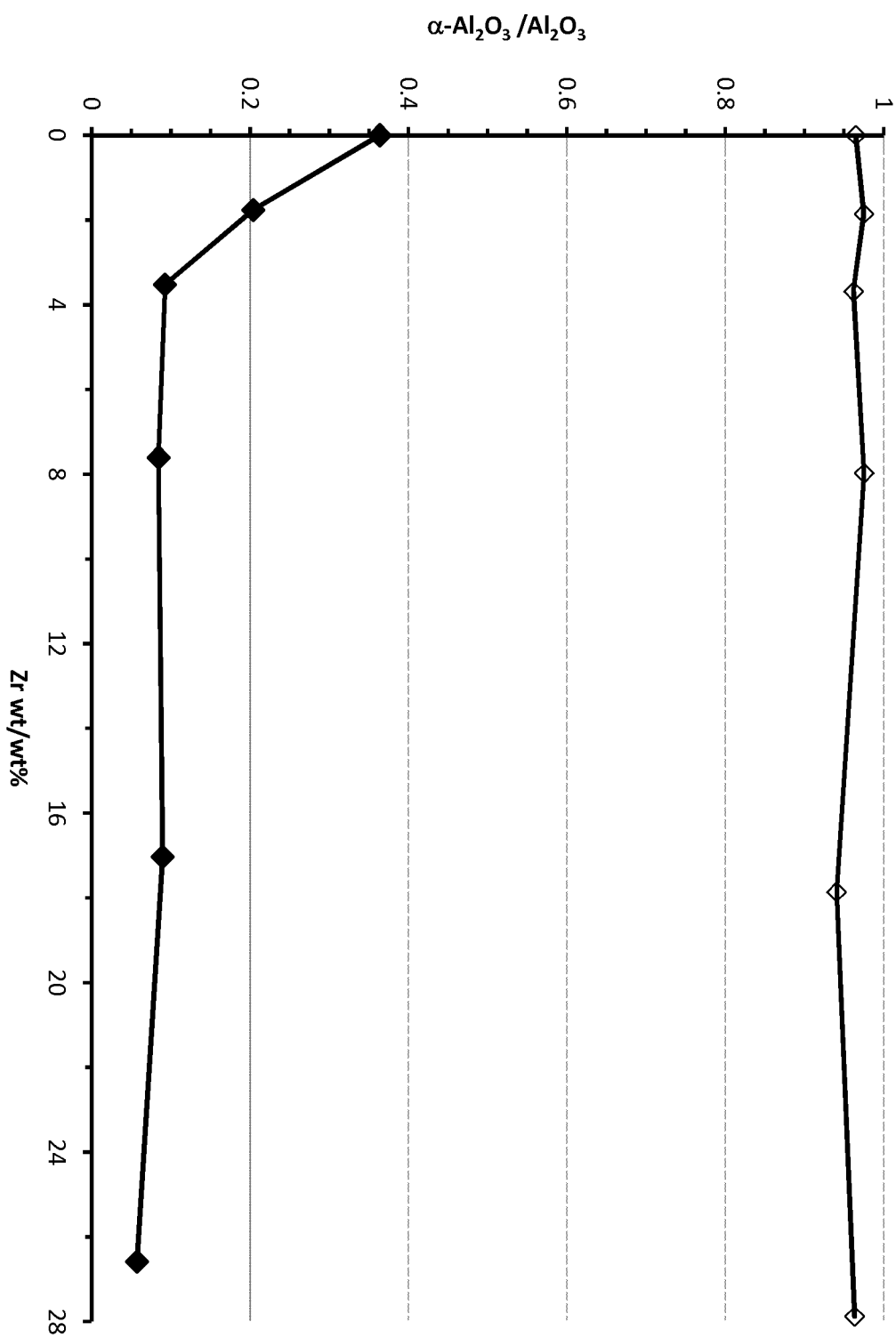
FIG. 2 is a graph showing the relative amount of alumina present as alpha alumina in the support (y-axis) vs. wt % $ZrO_2$ (x-axis).

For proper evaluation of the stability of a support to be used in methanation and reforming catalysts the proper test is the accelerated lab aging procedure described above. The relative amount of alumina which is present as alpha alumina in the support after the aging test is listed in Table 2. In FIG. 2 the relative amount of alumina which is present as alpha alumina in the support after the aging test is shown on the y-axis, as a function of composition. Open symbols correspond to supports I, J, K, L, M, N i.e. supports without presence of lanthanoides, and closed symbols correspond to supports O, P, Q, R, S, T i.e. with a presence of 4 wt % lanthanum as $La_2O_3$. The x-axis corresponds to the wt % $ZrO_2$.

The data of the calcined samples prior to aging testing show that for partial stabilization (61% conversion of transition alumina to alpha alumina) 27 wt % Zr is required in the absence of La, but this is not sufficient for stabilization during the accelerated long term aging test.

For an aged support stabilized with $La_2O_3$ but no $ZrO_2$ about 36% of the alumina is present as alpha alumina, but the stabilization synergy of $La_2O_3$ and $ZrO_2$ is already evident in the presence of 1.9 wt % Zr, where a significant stabilization is seen as only 20% of the alumina in the aged support is present as alpha alumina. For 3.7-27 wt % Zr the amount of alpha alumina is substantially constant at around 5-10 wt % indicating substantial stabilization of the transition alumina.

The graph therefore shows a strong synergy in the stabilization of transition alumina from the combined presence of oxides of zirconium and lanthanoides. The synergetic stabilization is very strong at combined elemental concentrations in the support of zirconium and lanthanoides from 4 wt %, and close to complete from 7 wt % or 10% wt/wt.

The invention claimed is:

1. A process for producing a gas rich in methane by reacting a synthesis gas comprising carbon oxide and hydrogen in the presence of a catalyst comprising a catalyst support comprising in oxide form: aluminum, zirconium, and one or more lanthanoid elements of the lanthanoid group of the periodic system, wherein at least a part of the aluminum is present as transition alumina selected from the group consisting of $\chi$, $\kappa$, $\gamma$, $\delta$, $\eta$, $\rho$ and $\theta$-alumina, and wherein the concentration of zirconium is at least 1.5 wt %, the concentration of lanthanoid is at least 0.5 wt %, and the combined concentration of zirconium and lanthanoid is at least 4 wt %.

2. The process according to claim 1 wherein the temperature of the synthesis gas prior to contacting the catalytically active material is from 200° C. to 800° C.

3. The process according to claim 1 wherein the temperature increase of the gas comprising methane after contacting the catalytically active material is at least 50° C.

4. The process according to claim 1, wherein the synthesis gas prior to contacting the catalytically active material has a molar ratio $M=(H_2-CO_2)/(CO+CO2)$ between 1 and 20.

5. The process according to claim 1, wherein the fraction of transition alumina in the support being $\chi$, $\kappa$, $\gamma$, $\delta$, $\eta$, $\rho$ and $\theta$-alumina is at least 0.1.

6. The process according to claim 1, wherein the one or more lanthanoid elements are selected from the group consisting of lanthanum, cerium, praseodymium, samarium, gadolinium, neodymium, europium, dysprosium and ytterbium.

7. The process according to claim 1, wherein the elemental concentration of the one or more lanthanoid elements present as oxide is at least 0.5 wt % and below 10 wt %.

8. The process according to claim 1, wherein the elemental concentration of zirconium is at least 1.5 wt % and below 50 wt %.

9. The process according to claim 1, wherein the catalyst support further comprises magnesium in an oxide form, in which the elemental concentration of magnesium is 1-30 wt %.

10. The process according to claim 1, wherein the catalyst comprises nickel in a concentration of 5-80 wt %.

* * * * *